(12) United States Patent
Den Hartog et al.

(10) Patent No.: US 7,851,630 B2
(45) Date of Patent: Dec. 14, 2010

(54) HYDRONOPOL SUBSTITUTED BENZIMIDAZOLONE AND QUINAZOLINONE DERIVATIVES AS AGONISTS ON HUMAN ORL1 RECEPTORS

(75) Inventors: Jacobus A. J. Den Hartog, Weesp (NL); Samuel David, Weesp (NL); Daniel Jasserand, Weesp (NL); Gustaaf J. M. Van Scharrenburg, Weesp (NL); Herman H. Van Stuivenberg, Weesp (NL); Tinka Tuinstra, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 1483 days.

(21) Appl. No.: 10/952,180

(22) Filed: Sep. 29, 2004

(65) Prior Publication Data

US 2005/0075355 A1 Apr. 7, 2005

Related U.S. Application Data

(60) Provisional application No. 60/507,947, filed on Oct. 3, 2003.

(30) Foreign Application Priority Data

Oct. 3, 2003 (EP) .................................. 03103671

(51) Int. Cl.
*C07D 211/58* (2006.01)
*A61K 31/454* (2006.01)

(52) U.S. Cl. ................... 546/199; 546/126; 544/293; 514/322; 514/266.22; 514/304

(58) Field of Classification Search ................. 514/310, 514/266.22, 322, 304; 546/199, 126; 544/293
See application file for complete search history.

(56) References Cited

U.S. PATENT DOCUMENTS

| | | | |
|---|---|---|---|
| 2005/0070528 A1* | 3/2005 | Den Hartog et al. | 514/221 |
| 2005/0131004 A1* | 6/2005 | Mentzel et al. | 514/278 |

FOREIGN PATENT DOCUMENTS

| | | | |
|---|---|---|---|
| EP | 1069124 A1 * | 1/2001 | |
| EP | 0 990 653 B1 | 9/2004 | |
| FR | 2 097 031 | 3/1972 | |
| WO | WO 99/36421 A1 | 7/1999 | |
| WO | WO 01/39775 A1 | 6/2001 | |

OTHER PUBLICATIONS

Zaveri et al., "Characterization of Opiates, Neuroleptics, and Synthetic Analogs at ORL1 and Opioid Receptors": *European Journal of Pharmacology*, 428:29-36 (2001).
Derwent Abstract for FR 2 097 031.
International Search Report for PCT Application No. PCT/EP2004/052392.

* cited by examiner

*Primary Examiner*—Rita J Desai
*Assistant Examiner*—David K O'Dell
(74) *Attorney, Agent, or Firm*—Finnegan, Henderson, Farabow, Garrett & Dunner, L.L.P.

(57) ABSTRACT

The invention relates to a group of hydronopol substituted benzimidazolone and quinazolinone derivatives which are agonists on human ORL1 (nociceptin) receptors. The invention also relates to the preparation of these compounds, to pharmaceutical compositions containing a pharmacologically active amount of at least one of these novel benzimidazolone and quinazolinone derivatives as an active ingredient, as well as to the use of these pharmaceutical compositions for the treatment of disorders in which ORL1 receptors are involved.

The invention relates to compounds of the general formula (1)

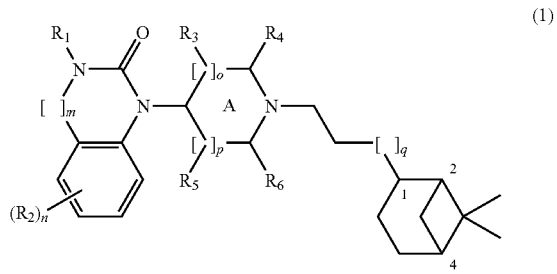

wherein the symbols have the meanings as given in the description.

6 Claims, No Drawings

HYDRONOPOL SUBSTITUTED BENZIMIDAZOLONE AND QUINAZOLINONE DERIVATIVES AS AGONISTS ON HUMAN ORL1 RECEPTORS

CROSS REFERENCE TO RELATED APPLICATION

This application claims the priority of European Application No. 03103671.8, filed Oct. 3, 2003, and claims the benefit of U.S. Provisional Application No. 60/507,947, filed Oct. 3, 2003, the content of which is incorporated herein by reference.

The present invention relates to a group of hydronopol substituted benzimidazolone and quinazolinone derivatives which are agonists on human ORL1 (nociceptin) receptors. The invention also relates to the preparation of these compounds, to pharmaceutical compositions containing a pharmacologically active amount of at least one of these novel benzimidazolone and quinazolinone derivatives as an active ingredient, as well as to the use of these pharmaceutical compositions for the treatment of disorders in which ORL1 receptors are involved.

The 'Opioid Receptor-Like 1' (ORL1) receptor was identified from a human cDNA library. It was established that this 'orphan receptor' has a close homology with μ-, κ- and δ-opioid receptors (Mollereau et al., *FEBS Lett.*, 341, 33-38, 1994; Bunzow et al., *FEBS Lett.*, 347, 284-288, 1994). Despite its close sequential and structural resemblance with opioid receptors, classical opioid receptor ligands do not to interact with ORL1 receptors. In 1995 a 17-amino acid neuropeptide was purified from brain extracts, and subsequently shown to be the natural ligand of the G protein-coupled ORL1 receptor (Reinscheid et al., *Science*, 270, 792-794, 1995; Meunier et al., *Nature*, 377, 532-535, 1995). This peptide was named orphanin FQ or nociceptin and it does not bind to the three traditional opioid receptors. These findings triggered substantial research into the functional role of, and novel ligands for, the ORL1 receptor. That resulted in several hundreds of publications, including several reviews (see e.g. Grond et al., *Anaesthesist*, 51, 996-1005, 2002), and dozens of patent applications, describing both peptide and non-peptide ligands, varying in potency and selectivity (ORL-1 versus μ-opiate). As μ-opiate receptors are widely distributed throughout the body, a lack of selectivity might lead to a range of undesired opiate-like side-effects e.g. sedation, respiratory depression, tolerance and dependence (*Drug News Perspect*, 14, 335, 2001). Six of the ORL1 related patent applications concern benzimidazolone derivatives: WO 98/54168, WO 99/36421, WO 00/006545, WO 00/08013, WO 01/39775 and US 20020128288.

The prior art closest to the present invention is WO 01/39775. However, the benzimidazolone derivatives described therein do not seem to meet the criteria generally acknowledged to be of importance for useful ORL1 based therapeutic agents. They are characterized by:
(1) modest potency (affinities for ORL1 receptors in the range of 166-1252 nM);
(2) lack of selectivity towards μ-opiate receptors (affinities in the range 19-457 nM);
(3) no evidence for availability after oral administration, and
(4) no evidence for CNS-availability.

Surprisingly, it has now been found that in a series of hydronopyl substituted benzimidazolone and quinazolinone derivatives, a group of compounds was shown to have a very high affinity for human ORL1 receptors. Moreover, these compounds show an excellent selectivity for ORL1 receptors relative to μ-opiate receptors, are readily available after oral administration and do penetrate the Blood-Brain-Barrier.

The invention relates to compounds of the general formula (1)

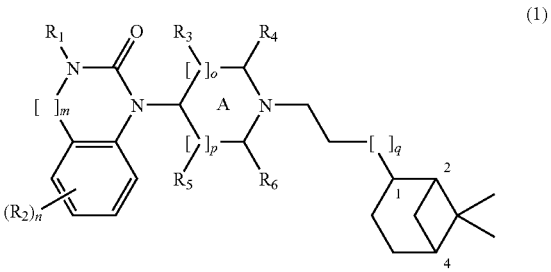

wherein:
$R_1$ represents H, alkyl(1-6C), alkyl(1-3C)cycloalkyl(3-6C), carbalkoxy(2-7C) or acyl(2-7C),
$[\ ]_m$ symbolizes —$(CH_2)_m$— wherein m is either 0 or 1,
$R_2$ represents halogen, $CF_3$, alkyl(1-6C), alkyl(1-3C)cycloalkyl(3-6C), phenyl, amino, aminoalkyl(1-3C), alkyl(1-3C)amino, dialkyl(1-3C)amino, cyano, cyanoalkyl(1-3C), hydroxy, hydroxyalkyl(1-3C), (1-3C)alkoxy, $OCF_3$, acyl (2-7C), trifluoroacetyl, aminocarboxyl, (1-3C)alkylsulphonyl or trifluoromethylsulphonyl, and n is an integer from 0-4, with the proviso that when n is 2, 3 or 4, the $R_2$ substituents may be either the same or different,
A is a saturated or partially unsaturated ring
$[\ ]_o$ and $[\ ]_p$ represent —$(CH_2)_o$— and —$(CH_2)_p$— respectively, with the proviso that also the meaning —CH— is possible when A is a partially unsaturated ring, and o and p independently are either 0, 1 or 2,
$R_3$, $R_4$, $R_5$ and $R_6$ independently represent hydrogen, alkyl(1-3C), alkyl(1-3C)-cycloalkyl(3-6C), $CH_2OH$ or ($R_3$ and $R_5$) or ($R_3$ and $R_6$) or ($R_4$ and $R_5$) or ($R_4$ and $R_6$) together can form an alkylene bridge of 1 to 3 carbon atoms, with the proviso that when o is 2, $R_3$ is hydrogen, and when p is 2, $R_5$ is hydrogen,
$[\ ]_q$ symbolizes —$(CH_2)_q$— wherein q is an integer from 0 to 2 and pharmacologically acceptable salts and prodrugs thereof.

To the invention belong all compounds having formula (1), racemates, mixtures of diastereomers and the individual stereoisomers. Thus compounds in which the substituents on potentially asymmetrical carbon atoms are in either the R-configuration or the S-configuration belong to the invention. Also prodrugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxymethylene derivative, an O-(acyloxymethylene carbamate) derivative, carbamate, ester, amide or enaminone. A prodrug is an inactive compound, which when absorbed is converted into an active form (Medicinal Chemistry: Principles and Practice, 1994, ISBN 0-85186-494-5, Ed.: F. D. King, p. 216).

The invention particularly relates to compounds having formula (1) wherein:
A is a saturated ring,
$R_1$ represents hydrogen, alkyl(1-3C), or acyl(2-4C),
$R_3$, $R_4$, $R_5$ and $R_6$ independently represent hydrogen or alkyl (1-3C) or ($R_3$ and $R_5$) or ($R_3$ and $R_6$) or ($R_4$ and $R_5$) or ($R_4$ and $R_6$) together can form an alkylene bridge of 1 to 3 carbon atoms, with the proviso that when o is 2, $R_3$ is hydrogen, and when p is 2, $R_5$ is hydrogen, and $R_2$, m, n, o, p and q have the meanings as given above.

More particular the invention relates to compounds of formula (1) wherein:

A is a saturated ring, m=0, n=0 or 1, o=1, p=1, q=0, $R_1$=H or acetyl, $R_2$ represents halogen, $CF_3$, alkyl(1-3C), amino, hydroxy, cyano, $OCH_3$ or $OCF_3$, $R_3$, $R_4$, $R_5$ and $R_6$ independently represent hydrogen or alkyl(1-2C) or ($R_4$ and $R_6$) together can form an alkylene bridge of 1 to 2 carbon atoms.

Even more preferred is the compound having formula (2) and all its stereoisomers.

The compounds of the invention and their salts can be obtained according to the general route outlined below.

scheme 1

X = Halogen, Mesylate, Tosylate

Starting compounds for this general route are obtained as follows:

Benzimidazolones (m=0) can be synthesized according to the methods described in *J. Med. Chem.,* 30, 814-819, 1987 and WO 99/36421 (Pfizer). Quinazolones (m=1) can be synthesized according to *Chem. Pharm. Bull.,* 33, 1116-1128, 1985. Hydronopol-derivatives with X as leaving group (halogen, mesylate, tosylate) can be synthesized from the corresponding alcohols following standard procedures. The corresponding alcohols can be synthesized as follows:

for the cis analog with q=0 from (−)-β-pinene as described in *J. Amer. Chem. Soc.* 68, 638, 1946 and U.S. Pat. Nos. 2,427,343 and 2,427,345 for the trans analog with q=0 from trans-myrtanol as described in *Bull. Soc. Chim. Fr.,* 196, 1958 or via a slightly alternative procedure (bromination of the alcohol, substitution by cyano, conversion to the ethylester and reduction to the desired alcohol)

for both the cis and trans analogs with q=1 or 2, by one or two cycles of an analogous homologation procedure as described for the synthesis of the trans analog with q=0 from trans-myrtanol.

Pharmaceutically acceptable salts may be obtained using standard procedures well known in the art, for example by mixing a compound of the present invention with a suitable acid, for instance an inorganic acid such as hydrochloric acid, or with an organic acid.

The compounds of the invention of the general formula (1), as well as the salts thereof, have ORL1 agonistic activity. They are useful in the treatment of disorders in which ORL1 receptors are involved, or that can be treated via manipulation of those receptors. For instance in acute and chronic pain conditions, central nervous system disorders, especially, but not limited to amelioration of symptoms of anxiety and stress disorders, depression, various forms of epilepsy, stroke, disorders characterized by impairment of cognition and memory such as Alzheimer's disease, Creutzfeldt-Jacob disease, Huntington's disease, Parkinson's disease, neurorehabilitation (post-traumatic brain lesions); acute brain or spinal cord injury, substance related disorders, including substance use disorders (like dependence and abuse) and substance induced disorders (like substance withdrawal); eating disorders like anorexia nervosa and bulimia nervosa, obesity; gastro-intestinal disorders in particular irritable bowel syndrome, inflammatory bowel disease (Crohn's disease and ulcerative colitis), urinary tract inflammation, renal disorders characterized by imbalances of water retention/excretion or salt excretion; cardiovascular disorders such as myocardial infarction, arrhythmias, hypertension, thrombosis, anaemia, arteriosclerosis, angina pectoris, cutaneous diseases such as urticaria, lupus erythematosus and pruritus; opthalmological disorders like glaucoma; respiratory disorders including cough, chronic obstructive pulmonary disease, bronchitis and cystic fibrosis; diseases of the immune system, and viral infections.

The in vitro and in vivo ORL1 receptor agonistic properties of the compounds of the invention were determined using the methods outlined below.

Affinity for Human ORL1 Receptors

Affinity of the compounds for human ORL1 receptors was determined using the in vitro receptor binding assay described by Ardati et al., *Mol. Pharmacol.,* 51, 816, 1997. Briefly, membrane preparations were obtained from CHO (Chinese Hamster Ovary)-cells in which the human ORL1 receptor was stably expressed. Membranes were incubated with [$^3$H]-nociceptin in the absence or presence of test-compounds in different concentrations, diluted in a suitable buffer. Non-specific binding was defined as binding remaining in the presence of $10^{-6}$ M nociceptin. Separation of bound radioactivity from free was done by filtration through Packard GF/B glass fiber filters with several washings with ice-cold buffer using a Packard cell harvester. Bound radioactivity was measured with a scintillation counter (Topcount, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_i$, values were calculated by correcting the $IC_{50}$ values for radioligand concentration and its affinity for the human ORL1 receptor according to the Cheng-Prusoff equation:

$$pK_i = -\log(IC_{50}/(1+S/K_d))$$

in which the $IC_{50}$ is as described above, S is the concentration [$^3$H]-nociceptin used in the assay expressed in mol/l (typically 0.2 nM), and $K_d$ is the equilibrium dissociation constant of [$^3$H]-nociceptin for human ORL1 receptors (0.4 nM).

The compounds of the invention have a high affinity for ORL1 receptors in the binding assay described above. This property makes them useful in the treatment of disorders in which ORL1 receptors are involved, or that can be treated via manipulation of these receptors.

Affinity for µ-Opiate Receptors

Affinity of the compounds for µ-opiate receptors was determined using the in vitro receptor binding assay described by Childers et al, *Eur. J. Pharm* 55, 11, 1979. Briefly, membrane preparations were obtained from CHO-cells in which the human µ-opiate receptor was stably expressed, and were incubated with the [$^3$H]-naloxone in the absence or presence of test-compounds in a concentration range from 10 uM down to 0.1 nM, diluted in a suitable buffer. Non specific binding was defined as binding remaining in the presence of $10^{-7}$ M levallorphan.tartrate. Separation of bound radioactivity from free was done as described above, and the affinity of the compounds was calculated in a similar way, using a concentration (S) of 1 nM [$^3$H]-naloxone and with a $K_d$ value of 1.3 nM.

Most of the compounds of the invention have a low affinity for µ-opiate receptors in the binding assay described above: typically a factor 100 below their affinity for ORL1 receptors. Thus they are unlikely to evoke the unwanted side effects known to occur with opiates like morphine.

In Vitro ORL1 Receptor Agonism

Activation of the G protein-coupled ORL1 receptor inhibits adenylate cyclase activity and reduces the intracellular concentration of the second messenger cAMP. Using the assay as described by Jenck et al., *Proc. Natl. Acad. Sci USA*, 97, 4938-4943, 2000, the activity of the compounds on ORL1 receptors was measured. They were demonstrated to be potent agonists with $pEC_{50}$-values matching their $pK_i$ values.

In Vivo ORL1 Receptor Agonism

After intraperitoneal and/or oral administration the compounds of the invention were shown to be highly active in the conditioned ultrasonic distress vocalisation procedure as described by Molewijk et al., *Psychopharmacology*, 117, 32-40, 1995. This demonstrates not only that the compounds have a good bioavailability after oral administration, but also that they cross the Blood-Brain-Barrier. The peptide nociceptine is also active in this assay, but in order to demonstrate its effect, it needs to be administered directly into the brain (by intracerebro-ventricular injection).

SPECIFIC EXAMPLES OF SYNTHESES

Synthesis of Example 1 (See Table Below)

Step 1. A solution of (−)-cis hydronopol (20 g, 0.12 mole) and triethylamine (41.6 ml, 0.30 mole) in dichloromethane (150 ml) was cooled to 0° C. and under ice-cooling a solution of mesylchloride (11.2 ml, 0.15 mole) in dichloromethane (50 ml) was dropwise added. After stirring at room temperature for 16 hours a solution of HCl (1N, 100 ml) was added. The aqueous layer was washed twice with 70 ml dichloromethane, and the combined organic layers were dried over magnesium sulphate and concentrated in vacuo. The mesylate was obtained as a yellow orange coloured oily product (27.7 g, 11 mole, 92% yield).

Step 2. A stirred solution of 4-(1-benzimidazolone)piperidine (ACROS, 6.51 g, 30 mmole), the mesylate obtained in the previous reaction step (8.9 g, 36 mmole), potassium carbonate (16.8 g, 120 mmole) and sodium iodide (5.4 g, 36 mmole) in methyl ethyl ketone (800 ml) was heated under $N_2$ at 80° C. for 16 hours. After concentration of the reaction mixture in vacuo, dichloromethane (500 ml) and aqueous $NaHCO_3$ (5%, 300 ml) were added. The aqueous layer was washed with dichloromethane (2 times 80 ml) and the combined organic layers were dried over $MgSO_4$ and concentrated in vacuo. The crude product was purified by column chromatography (silicagel) with a mixture of dichloromethane:methanol:ammonia (94.5:5:0.5) as the eluent. A solution of the pure product resulting after concentration in vacuo (7.5 g, 20 mmole, 68% yield) was dissolved in a solution of HCl in absolute ethanol (60 ml). Concentration in vacuo of the resulting solution at 30° C. afforded the HCl salt of example 1 (8.25 g, 20 mmole, quantitative yield) as a white amorphous solid with a $M^+$ of 368 m/z and a melting point of 167-174° C.

Synthesis of Example 43

Step 1. Triphenylphosphine (116 g, 0.44 mole) was dissolved in acetonitrile (1 liter) and cooled in an ice bath under $N_2$ atmosphere. Bromine (22.5 ml, 0.44 mole) was added dropwise. The temperature of the exothermic reaction was maintained below 10° C. After complete addition the ice bath was removed and (−)-trans-myrtanol (68.8 g, 0.44 mole, Aldrich) dissolved in 250 ml acetonitrile was slowly added. After complete addition the light yellow solution was refluxed for 3 hours using a Dean-Stark equipment, under removal of about 200 ml of solvent from the water trap. The resulting reaction mixture was concen-trated in vacuo. The crude product was purified by column chromatography (silicagel) with a mixture of dichloromethane-diethylether (1:1 v/v) as the eluent. The pure product was obtained as a light yellow oil (87.8 g, 41 mmole, 93% yield).

Step 2. The obtained myrtanylbromide (87.8 g, 0.41 mole) was dissolved in 1 liter dimethylformamide. Sodium cyanide (40 g, 0.81 mole) was added and the mixture was stirred at reflux for 5 hours. After cooling the mixture was diluted with water (3 liter) and extracted with methyl t-butyl ether (3 times 1.5 liter). The organic layer was washed with brine (300 ml), dried over $Na_2SO_4$ and concentrated in vacuo. The crude product was purified by column chroma-tography (silicagel) with a mixture of dichloromethane-heptane (1:1 v/v) as the eluent. The pure product was obtained as a colorless liquid (52.4 g, 0.32 mole, 78% yield).

Step 3. Sulphuric acid (190 ml) was added dropwise to 500 ml ethanol cooled in an ice bath. A solution of the obtained myrtanyl cyanide (52.4 g, 0.32 mole) in ethanol (100 ml) was added and the mixture was stirred at reflux for 16 hours. After cooling and addition of 1.5 liter water, the mixture was extracted three times with 1.5 liter methyl t.butyl ether. The organic layer was washed with saturated aqueous $NaHCO_3$ (1 liter), dried over $Na_2SO_4$ and concentrated in vacuo. The crude ester (54.2 g, 0.26 mole, 81% yield) was obtained as a nearly colorless liquid.

Step 4. The ester obtained in the previous reaction step (54.2 g, 0.26 mole) was added to a suspension of lithium aluminium hydride (20 g, 0.52 mole) in tetrahydrofuran (1 liter). After complete addition the mixture was refluxed for 1 hour. After cooling in an ice bath 1 liter of aqueous HCl (1N) was carefully added. After complete addition, the mixture was further diluted with 1 liter of water and three times extracted with 1.5 liter methyl t-butyl ether. The organic layer was washed with brine (250 ml), dried over $Na_2SO_4$ and concentrated in vacuo. The crude mixture was purified by Kugelrohr distillation (bp 85° C. at $3.10^{-2}$ mbar) giving 35 g (0.17 mole, 65%) of the (−)-trans hydronopol as a colourless oil.

Step 5. A solution of the prepared (−)-trans hydronopol (5 gr, 28 mmole) and triethylamine (9.4 ml, 68 mmole) in dichloromethane (50 ml) was cooled to 0° C. Under ice-cooling a solution of mesylchloride (2.7 ml, 35 mmole) in dichloromethane (13 ml) was dropwise added. After stirring at room temperature for 16 hours a solution of HCl (1N, 50 ml) was added. The aqueous layer was washed with dichloromethane (2 times 30 ml) and the combined organic layers were dried over magnesium sulphate and concentrated in vacuo. The mesylate was purified by column chromatography (silicagel) with a mixture of dichloromethane-methanol (90: 10) as the eluent. The pure product was obtained as a colorless liquid (5.6 g, 23 mmole, 81% yield).

Step 6. A stirred solution of 4-(1-benzimidazolone) piperidine (ACROS, 1.8 g, 8.3 mmole), the mesylate obtained in the previous reaction step (2.5 g, 10 mmole), potassium carbonate (4.7 g, 34 mmole) and sodium iodide (1.5 g, 10 mmole) in methyl ethyl ketone (300 ml) was heated under $N_2$ at 80° C. for 16 hours. After concentration of the reaction mixture in vacuo, diisopropylether (300 ml) was added. The obtained light yellow precipitate was filtered off, washed with petroleum ether (100 ml) ands dried in vacuo. The precipitate was once more dissolved in refluxing ether (300 ml) and filtered to remove base-line material. The precipitate obtained after cooling was collected by filtration and dried in vacuo to give 1.85 g, (5 mmole, 61% yield) of the pure product as a white amorphous solid with a $M^+$ of 368 m/z and a melting range of 220-239° C.

Synthesis of Example 17

Step 1. A solution of 3-fluoro-4-nitrotoluene (Aldrich, 4.65 gr, 30 mmole), 4-amino-1-benzyl-piperidine (Aldrich, 6.1 ml, 30 mmole), $K_2CO_3$ (6.63 gr, 48 mmole) in dimethylformamide (50 ml) was stirred at 65° C. under $N_2$ for 18 hours. After cooling to room temperature the mixture was poured into water (200 ml)-dichloromethane (350 ml). The aqueous layer was extracted with dichloromethane (two times 70 ml) and the combined organic layers were washed with water (two times 50 ml), dried over $MgSO_4$ and concentrated in vacuo. The resulting crude product was purified by column chromatography (silicagel) with a mixture of dichloromethane-methanol (97:3) as the eluent. After concentration in vacuo the pure product was obtained as a yellow oily substance (9.1 gr, 28 mmole, 93% yield).

Step 2. A portion of Raney-Ni (Aldrich R 2800 [7440-02-0], approximately 600 mg) was washed with 96% ethanol (twice 10 ml) and subsequently added under $N_2$ to a solution of the product from the previous reaction step (9.1 g, 28 mmole) in 96% ethanol (200 ml). The solution was hydrogenated at room temperature and a pressure of 1 atmosphere for 18 hours. The mixture was subsequently filtered over Hyflo, washed with 96% ethanol (3 times 100 ml) and the filtrate concentrated in vacuo and two times co-evaporated with ethyl acetate to give the reduced product as a purple oily substance (8.3 g, 28 mmole, 100% yield).

Step 3. To a solution of the product from the previous step (8.3 g, 28 mmole) in acetonitrile (100 ml), stirred at room temperature under nitrogen, a portion of 1,1'-carbonyldiimidazole (ACROS, 6.5 g, 40 mmole) was added. The precipitate, starting to form at 5 minutes and increasing up to 3 hours, was collected by filtration, washed with acetonitrile (20 ml) and diisopropylether (100 ml) and dried in vacuo. The crude product (5.5 g) was purified by column chromatography (silicagel) with a mixture of dichloromethane-methanol (95:5) as the eluent. After concentration in vacuo the pure product was obtained as a white solid (5.0 g, 15 mmole, 55% yield).

Step 4. To a solution of 5.0 g (15 mmole) of the product from the previous step in 300 ml methanol stirred under $N_2$, a 1N alcoholic HCl solution (prepared from 1.22 g (15 mmole) acetyl chloride in 50 ml absolute ethanol) was added. After addition of 10% Pd/C (approximately 500 mg) the mixture was hydrogenated at room temperature and a pressure of 1 atmosphere for 2½ hours. The mixture was subsequently filtered over Hyflo, washed with methanol (2 times 100 ml) and the filtrate concentrated in vacuo, giving 4.15 g (15 mmole, 100% yield) of the product as a white solid.

Step 5. A stirred solution of the product from the previous step (4.15 g, 15 mmole), the mesylate from Step 1 of Example 1 (8.9 g, 16 mmole), potassium carbonate (10.4 g, 75 mmole) and sodium iodide (2.4 g, 16 mmole) in methyl ethyl ketone (250 ml) was heated under $N_2$ at 80° C. for 16 hours. After concentration of the reaction mixture in vacuo, dichloromethane (500 ml) and aqueous $NaHCO_3$ (5%, 300 ml) were added. The aqueous layer was washed with dichloromethane (2 times 80 ml) and the combined organic layers were dried over $MgSO_4$ and concentrated in vacuo. The crude product was purified by column chromatography (silicagel) with a mixture of dichloromethane-methanol-ammonia (92:7.5:0.5) as the eluent. Concentration in vacuo gave the pure product (5.0 g, 13 mmole) as an oily substance. After addition of 100 ml diisopropylether to this oil and stirring at room temperature for 30 minutes, the product precipitated as a white solid. The solid was collected by filtration and dried in vacuo to give 3.3 g (8.6 mmole, 57% yield) with a $M^+$ of 382 m/z and a melting point of 214-217° C.

By these and comparable methods, 45 specific examples were synthesized. They are intended to further illustrate the invention in more detail, and therefore are not deemed to restrict the scope of the invention in any way. Structural information of these compounds, all represented by the general formula (1), is presented in the table below.

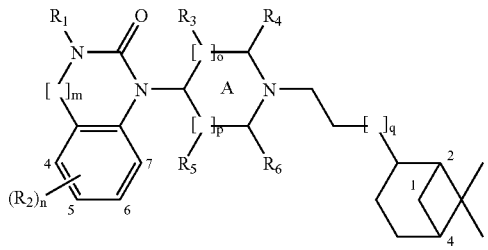

(1)

| nr | R$_1$ | m | R$_2$ | n | A | o | p | R$_3$ | R$_4$ | R$_6$ | R$_5$ | q | 1 | 2 | 4 |
|---|---|---|---|---|---|---|---|---|---|---|---|---|---|---|---|
| 1 | H | 0 | — | 0 | sat | 1 | 1 | H | H | H | H | 0 | S | S | S |
| 2 | H | 1 | — | 0 | sat | 1 | 1 | H | H | H | H | 0 | S | S | S |
| 3 | CH$_3$ | 0 | — | 0 | sat | 1 | 1 | H | H | H | H | 0 | S | S | S |
| 4 | CH$_3$ | 1 | — | 0 | sat | 1 | 1 | H | H | H | H | 0 | S | S | S |
| 5 | H | 0 | 4-F | 1 | sat | 1 | 1 | H | H | H | H | 0 | S | S | S |
| 6 | H | 0 | 5-F | 1 | sat | 1 | 1 | H | H | H | H | 0 | S | S | S |
| 7 | H | 0 | 6-F | 1 | sat | 1 | 1 | H | H | H | H | 0 | S | S | S |
| 8 | H | 0 | 7-F | 1 | sat | 1 | 1 | H | H | H | H | 0 | S | S | S |
| 9 | H | 0 | 5-CF$_3$ | 1 | sat | 1 | 1 | H | H | H | H | 0 | S | S | S |
| 10 | H | 0 | 6-CF$_3$ | 1 | sat | 1 | 1 | H | H | H | H | 0 | S | S | S |
| 11 | H | 0 | 4-Cl | 1 | sat | 1 | 1 | H | H | H | H | 0 | S | S | S |
| 12 | H | 0 | 5-Cl | 1 | sat | 1 | 1 | H | H | H | H | 0 | S | S | S |
| 13 | H | 0 | 6-Cl | 1 | sat | 1 | 1 | H | H | H | H | 0 | S | S | S |
| 14 | H | 0 | 7-Cl | 1 | sat | 1 | 1 | H | H | H | H | 0 | S | S | S |
| 15 | H | 0 | 4-CH$_3$ | 1 | sat | 1 | 1 | H | H | H | H | 0 | S | S | S |
| 16 | H | 0 | 5-CH$_3$ | 1 | sat | 1 | 1 | H | H | H | H | 0 | S | S | S |
| 17 | H | 0 | 6-CH$_3$ | 1 | sat | 1 | 1 | H | H | H | H | 0 | S | S | S |
| 18 | H | 0 | 7-CH$_3$ | 1 | sat | 1 | 1 | H | H | H | H | 0 | S | S | S |
| 19 | H | 0 | 4-OCH$_3$ | 1 | sat | 1 | 1 | H | H | H | H | 0 | S | S | S |
| 20 | H | 0 | 5-OCH$_3$ | 1 | sat | 1 | 1 | H | H | H | H | 0 | S | S | S |
| 21 | H | 0 | 6-OCH$_3$ | 1 | sat | 1 | 1 | H | H | H | H | 0 | S | S | S |
| 22 | H | 0 | 6-OH | 1 | sat | 1 | 1 | H | H | H | H | 0 | S | S | S |
| 23 | H | 0 | 6-NHCOCH$_3$ | 1 | sat | 1 | 1 | H | H | H | H | 0 | S | S | S |
| 24 | H | 0 | 6-CN | 1 | sat | 1 | 1 | H | H | H | H | 0 | S | S | S |
| 25 | H | 0 | 6-CH$_2$CN | 1 | sat | 1 | 1 | H | H | H | H | 0 | S | S | S |
| 26 | H | 0 | 6-SO$_2$CH$_3$ | 1 | sat | 1 | 1 | H | H | H | H | 0 | S | S | S |
| 27 | H | 0 | 6-SO$_2$CF$_3$ | 1 | sat | 1 | 1 | H | H | H | H | 0 | S | S | S |
| 28 | H | 0 | 6-COCH$_3$ | 1 | sat | 1 | 1 | H | H | H | H | 0 | S | S | S |
| 29 | H | 0 | 6-COCF$_3$ | 1 | sat | 1 | 1 | H | H | H | H | 0 | S | S | S |
| 30 | H | 0 | 6-CONH$_2$ | 1 | sat | 1 | 1 | H | H | H | H | 0 | S | S | S |
| 31 | H | 0 | 6-OCF$_3$ | 1 | sat | 1 | 1 | H | H | H | H | 0 | S | S | S |
| 32 | H | 0 | 6,7-F | 2 | sat | 1 | 1 | H | H | H | H | 0 | S | S | S |
| 33 | H | 0 | 4-F,6-OCH$_3$ | 2 | sat | 1 | 1 | H | H | H | H | 0 | S | S | S |
| 34 | H | 0 | 4-CH$_3$,6-OCH$_3$ | 2 | sat | 1 | 1 | H | H | H | H | 0 | S | S | S |
| 35 | H | 0 | — | 0 | uns | 1 | 1 | H | H | H | H | 0 | S | S | S |
| 36 | H | 0 | — | 0 | sat | 1 | 0 | H | H | H | H | 0 | S | S | S |
| 37 | H | 0 | — | 0 | sat | 0 | 0 | H | H | H | H | 0 | S | S | S |
| 38 | H | 0 | — | 0 | sat | 1 | 1 | CH$_3$ | H | H | H | 0 | S | S | S |
| 39 | H | 0 | — | 0 | sat | 1 | 1 | H | CH$_3$ | H | H | 0 | S | S | S |
| 40 | H | 0 | — | 0 | sat | 1 | 1 | H | H | H | CH$_3$ | 0 | S | S | S |
| 41 | H | 0 | — | 0 | sat | 1 | 1 | H | H | CH$_3$ | H | 0 | S | S | S |
| 42 | H | 0 | — | 0 | sat | 1 | 1 | H | —CH$_2$—CH$_2$— | | H | 0 | S | S | S |
| 43 | H | 0 | — | 0 | sat | 1 | 1 | H | H | H | H | 0 | R | S | S |
| 44 | H | 0 | — | 0 | sat | 1 | 1 | H | H | H | H | 1 | S | S | S |
| 45 | H | 0 | — | 0 | sat | 1 | 1 | H | H | H | H | 1 | R | S | S |

EXAMPLE OF FORMULATION OF COMPOUND AS USED IN ANIMAL STUDIES

Formulation of Example 1

For oral (p.o.) administration: to the desired quantity (0.5-5 mg) of the solid Example 1 in a glass tube, some glass beads were added and the solid was milled by vortexing for 2 minutes. After addition of 1 ml of a solution of 1% Methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid Example 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Pharmacological Data

| | affinity | | In vitro agonism | In vivo agonism C.U.D.V.* | |
|---|---|---|---|---|---|
| | | | | i.p. | p.o. |
| Ex. | ORL1 p$K_i$ | μ-opiate p$K_i$ | cAMP assay p$EC_{50}$ | $ED_{50}$ mg/kg | $ED_{50}$ mg/kg |
| 1 | 8.4 | 7.2 | 8.6 | 1.4 | 6.0 |
| 2 | 7.8 | 7.3 | 8.5 | 7.4 | |

*CUDV = Conditioned Ultrasonic Distress Vocalisation;
i.p. = intraperitoneal administration;
p.o. = (per os) oral administration.

The invention claimed is:

1. A compound of formula (1)

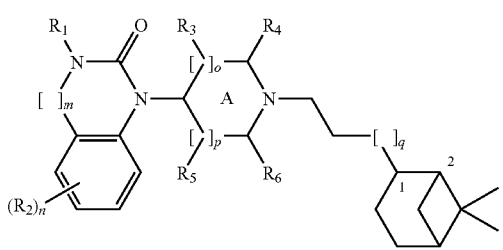

or a pharmaceutically acceptable salt, or a stereoisomer of any of the foregoing
wherein:
R1 is chosen from H, alkyl(1-6C), alkyl(1-3C)cycloalkyl (3-6C), carbalkoxy(2-7C) and acyl(2-7C);
$[\ ]_m$ symbolizes —$(CH_2)_m$— wherein m is chosen from 0 and 1;
$R_2$ is chosen from halogen, $CF_3$, alkyl(1-6C), alkyl(1-3C) cycloalkyl(3-6C), phenyl, amino, aminoalkyl(1-3C), alkyl(1-3C)amino, dialkyl(1-3C)-amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulphonyl and trifluoromethylsulphonyl, and n is an integer ranging from 0 to 4, with the proviso that when n is 2, 3 or 4, the $R_2$ substituents may be either the same or different;
A is chosen from saturated and partially unsaturated rings;
$[\ ]_o$ and $[\ ]_p$ symbolize —$(CH_2)_o$— and —$(CH_2)_p$— respectively, with the proviso that —CH— is possible when A is a partially unsaturated ring, and o and p independently are chosen from 0, 1 and 2;
$R_3$, $R_4$, $R_5$ and $R_6$, which are different or identical, are chosen from hydrogen, alkyl(1-3C), alkyl(1-3C)-cycloalkyl(3-6C), $CH_2OH$ and ($R_3$ and $R_5$) or ($R_3$ and $R_6$) or ($R_4$ and $R_5$) or ($R_4$ and $R_6$) together can form an alkylene bridge of 1 to 3 carbon atoms, with the proviso that when o is 2, $R_3$ is hydrogen, and when p is 2, $R_5$ is hydrogen; and
$[\ ]_q$ symbolizes —$(CH_2)_q$— wherein q is an integer ranging form 0 to 2.

2. The compound as claimed in claim 1, wherein
A is a saturated ring;
$R_1$ is chosen from hydrogen, alkyl(1-3C), and acyl(2-4C);
$R_3$, $R_4$, $R_5$ and $R_6$, which are different or identical, are chosen from hydrogen, alkyl(1-3C), and ($R_3$ and $R_5$) or ($R_3$ and $R_6$) or ($R_4$ and $R_5$) or ($R_4$ and $R_6$) together can form an alkylene bridge of 1 to 3 carbon atoms, with the proviso that when o is 2, $R_3$ is hydrogen, and when p is 2, $R_5$ is hydrogen.

3. The compound as claimed in claim 1, wherein
A is a saturated ring;
m is 0; n is 0 or 1; o is 1; p is 1; $R_1$ is chosen from hydrogen and acetyl;
$R_2$ is chosen from halogen, CF3, alkyl(1-3C), amino, hydroxy, cyano, $OCH_3$ and $OCF_3$;
$R_3$, $R_4$, $R_5$ and $R_6$, which are different or identical, are chosen from hydrogen, alkyl(1-2C), and ($R_4$ and $R_6$) together can form an alkylene bridge of 1 to 2 carbon atoms.

4. The compound as claimed in claim 1, wherein the compound of formula (1) is a compound of formula (2) or a stereoisomer thereof:

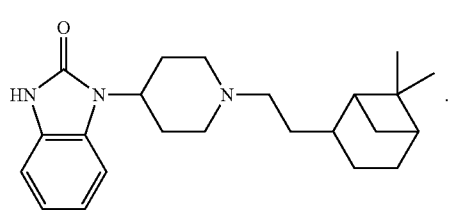

5. A pharmaceutical composition comprising a pharmacologically active amount of at least one compound of formula (I)

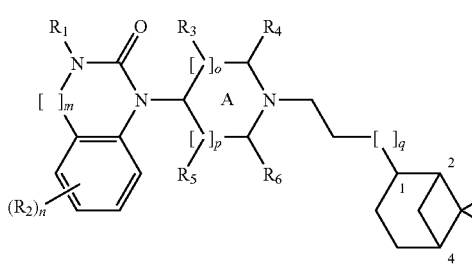

or a pharmaceutically acceptable salt, or a stereoisomer of any of the foregoing
wherein:
R1 is chosen from H, alkyl(1-6C), alkyl(1-3C)cycloalkyl (3-6C), carbalkoxy(2-7C) and acyl)(2-7C);
$[\ ]_m$ symbolizes —$(CH_2)_m$— wherein m is chosen from 0 and 1;
$R_2$ is chosen from halogen, $CF_3$, alkyl(1-6C), alkyl(1-3C) cycloalkyl(3-6C), phenyl, amino, aminoalkyl(1-3C), alkyl(1-3C)amino, dialkyl(1-3C)-amino, cyano, cyanoalkyl(1-3C), hydroxy, hydroxyalkyl(1-3C), (1-3C)alkoxy, $OCF_3$, acyl(2-7C), trifluoroacetyl, aminocarboxyl, (1-3C)alkylsulphonyl and trifluoromethylsulphonyl, and n is an integer ranging from 0 to 4, with the proviso that when n is 2, 3 or 4, the $R_2$ substituents may be either the same or different;
A is chosen from saturated and partially unsaturated rings;
$[\ ]_o$ and $[\ ]_p$ symbolize —$(CH_2)_o$— and —$(CH_2)_p$— respectively, with the proviso that —CH— is possible when A is a partially unsaturated ring, and o and p independently are chosen from 0, 1 and 2;

$R_3$, $R_4$, $R_5$ and $R_6$, which are different or identical, are chosen from hydrogen, alkyl(1-3C), alkyl(1-3C)-cycloalkyl(3-6C), $CH_2OH$ and ($R_3$ and $R_5$) or ($R_3$ and $R_6$) or ($R_4$ and $R_5$) or ($R_4$ and $R_6$) together can form an alkylene bridge of 1 to 3 carbon atoms, with the proviso that when o is 2, $R_3$ is hydrogen, and when p is 2, $R_5$ is hydrogen; and $[\ ]_q$ symbolizes —$(CH_2)_q$— wherein q is an integer ranging form 0 to 2.

6. A medicament comprising a compound as claimed in claim 1, or a pharmaceutically acceptable salt thereof.

* * * * *